United States Patent [19]

Ryan et al.

[11] Patent Number: 4,867,971

[45] Date of Patent: Sep. 19, 1989

[54] LOW PH SHAMPOO CONTAINING CLIMBAZOLE

[75] Inventors: Joyce Ryan, Breightmet; Malcolm Stansfield, Prestwich, both of England

[73] Assignee: Colgate-Palmolive Company, Piscataway, N.J.

[21] Appl. No.: 185,583

[22] Filed: Apr. 22, 1988

[51] Int. Cl.$^4$ .................... A61K 31/74; A61K 31/78; A61K 7/06; A01N 43/50

[52] U.S. Cl. ........................................ 424/81; 424/78; 424/70; 514/399; 514/852

[58] Field of Search .................... 424/78, 81; 514/399, 514/852

[56] References Cited

U.S. PATENT DOCUMENTS

| | | | |
|---|---|---|---|
| 3,658,985 | 4/1972 | Olson et al. | 424/70 |
| 3,812,142 | 5/1974 | Meiser et al. | 260/309 |
| 3,903,287 | 9/1975 | Meiser et al. | 424/273 |
| 4,321,156 | 5/1982 | Bushman | 252/142 |
| 4,329,334 | 5/1982 | Su et al. | 424/70 |
| 4,329,335 | 5/1982 | Su et al. | 424/70 |
| 4,329,336 | 5/1982 | Su et al. | 424/70 |
| 4,457,938 | 7/1984 | von Bitters et al. | 424/273 |
| 4,581,351 | 4/1986 | Berke et al. | 514/188 |
| 4,636,329 | 1/1987 | Steuri | 252/106 |

FOREIGN PATENT DOCUMENTS

| | | | |
|---|---|---|---|
| 0202621 | 5/1985 | European Pat. Off. | 424/70 |
| 0160269 | 11/1985 | European Pat. Off. | |
| 1502144 | 5/1975 | United Kingdom | 424/70 |
| 2161172A | 1/1986 | United Kingdom | |

*Primary Examiner*—Joseph L. Schofer
*Assistant Examiner*—C. Pili-Curtis
*Attorney, Agent, or Firm*—Richard J. Ancel; Murray M. Grill; Robert C. Sullivan

[57] ABSTRACT

A stable homogeneous liquid antidandruff shampoo comprising about 0.10 to 2.0% by weight of 1-imidazolyl-1-(4-chlorophenoxy)-3,3-dimethylbutan-2-one (Climbazole) solubilized in an aqueous vehicle containing an acidic surfactant system of about pH 4 to pH 5.5 and further comprising a major amount of an anionic surfactant and minor amounts of either a nonionic, cationic, or amphoteric surfactant or a mixture thereof.

21 Claims, No Drawings

LOW PH SHAMPOO CONTAINING CLIMBAZOLE

BACKGROUND OF THE INVENTION AND PRIOR ART

This invention relates to an antidandruff shampoo containing a low pH surfactant system and Climbazole which provides increased deposition of Climbazole on the skin and enhanced antidandruff efficacy. This increased antidandruff efficacy is believed to be the result of increased deposition of Climbazole to the skin at a reduced pH of about 4–5.

The prior art discloses the imidazolyl ketones such as 1-imidazolyl-1-(4-chlorophenoxy)-3,3-dimethylbutan-2-one, in U.S. Pat. Nos. 3,812,142 and 3,903,287 as antimycotic agents, useful in pharmaceutical compositions including aqueous suspensions containing surface active agents such as polyoxyethylene sorbitan fatty acid esters. British Pat. No. 1,502,144 and its German counterpart, Pat. No. 2,430,039, disclose cosmetic compositions such as shampoos containing the imidazolyl ketone antimycotic agents dispersed in a dermatologically acceptable carrier in the form of creams, aerosols, powders and liquids. Although the shampoo formulas disclosed on pages 35–36 of the British patent do not specify pH, a dermatologically acceptable carrier would have a pH of about 5.5–6.5 (skin pH). This is substantiated by the disclosure on page 27 in which a test of the shampoo against Pityrosporum is conducted at pH 6.4.

Also disclosed in the prior art are surfactant based antimicrobial shampoos containing Climbazole and having a pH of 6.5 to 7.5, as shown in U.S. Pat. Nos. 4,329,334; 4,329,335; and 4,329,336.

U.S. Pat. No. 4,457,938 discloses a stick formulation containing 0.05–1.0% of an antimycotic azole derivative such as Climbazole.

U.S. Pat. No. 3,658,985 discloses a liquid shampoo containing an aqueous detergent composition, an oil and a fluorescent dye adjusted to a pH relatively close to neutral, preferably a pH of 6.5–8.5. No Climbazole ingredient is disclosed therein.

Shampoos having acidic pH of 3 to 4.5 are disclosed in U.S. Pat. No. 4,321,156, having a pH of 2 to 4 in U.S. Pat. No. 4,636,392, having a pH of 5 to 7.5 in European patent application No. 0,160,269, and having a pH of 5 to 7 in British Pat. No. 2,161,172A. All of the aforesaid shampoos are mild conditioning shampoos containing various combinations of surfactants. No antidandruff agent is disclosed in these shampoo compositions.

European patent application No. 0202621 discloses a clear therapeutic hair care composition having a pH of 3 to 6.5 and preferably 4.9 to 5.7 containing a detergent shampoo base, a keratolytic agent such as a salicylate, and a stabilizing agent such as tertiary amines, ascorbic acid and sodium sulfite, to stabilize said salicylate against oxidative decoloration decomposition.

However, there is no disclosure of an antidandruff liquid shampoo comprising a low pH of about 4 to 5, and a surfactant system containing about 0.10 to 2.00% by weight of the imidazolyl ketone antidandruff agent, namely Climbazole, and a water soluble surfactant system comprising an anionic surfactant and a minor amount of either a nonionic, cationic or amphoteric surfactant or a mixture thereof.

SUMMARY OF THE INVENTION

It has now been found that antidandruff shampoos containing a low level of Climbazole and a low pH surfactant system of about pH 4 to pH 5.5 provides increased deposition of Climbazole on the skin and enhanced antidandruff efficacy. The increased deposition of Climbazole on the skin is believed to provide improved clinical efficacy and considerable cost saving. Lesser amounts of Climbazole in shampoos at low pH provide a considerably greater amount of Climbazole deposition to the skin than greater amounts of Climbazole at the standard pH 7.0. Clinical tests have clearly shown that a decrease in the pH of a shampoo down to pH 4.0 increases the amount of Climbazole deposited and adhering to the skin. It has also been demonstrated that a 1% Climbazole shampoo at pH 4.0 is significantly better at reducing dandruff than either a 1% Climbazole shampoo at pH 7.0 or the current U.S. Head and Shoulders shampoo.

Accordingly, it is a primary object of the present invention to provide a stable liquid Climbazole-containing antidandruff shampoo which provides increased deposition of Climbazole on the skin and enhanced antidandruff efficacy.

Another object of the present invention is to provide low level Climbazole antidandruff shampoos which are effective at a low pH.

Still another object of the present invention is to provide low level Climbazole antidandruff shampoos which are effective at low pH when used once or twice weekly.

Additional objects, advantages and novel features of the invention will be set forth in part in the description which follows, and will become apparent to those skilled in the art upon examination of the following specification or may be learned by practice of the invention.

To achieve the foregoing and other objects in accordance with the present invention, as embodied and broadly described herein, the stable homogeneous liquid antidandruff shampoo composition of this invention comprises an effective antidandruff amount of about 0.12–2% and preferably 0.5–2% by weight of 1-imidazolyl-1-(4-chlorophenoxy)-3,3-dimethylbutan-2-one solubilized in an aqueous vehicle containing a low pH surfactant system of about pH 4–5.5, preferably pH 4–5, comprising a water-soluble anionic surfactant as the primary surfactant and a minor amount of a supplemental surfactant selected from the group consisting of nonionic, cationic and amphoteric surfactants, and mixtures thereof.

More specifically the present invention relates to a liquid antidandruff shampoo having a pH of about 4–5 consisting essentially of about 0.10–2% by weight of 1-imidazolyl-1-(4-chlorophenoxy)-3,3,-dimethylbutan-2-one solubilized in about 70–95% by weight of an aqueous vehicle containing a water soluble surfactant system comprising about 6–25% by weight of an anionic surfactant and about 1–7% by weight of the supplemental surfactant or mixture of surfactants. A preferred additional ingredient is a triethanolamine myristate in an amount of about 4% by weight.

DETAILED DESCRIPTION OF THE INVENTION

The antidandruff agent utilized in the instant invention is 1-imidazolyl-1-(4-clorophenoxy)-3,3-dimethylbutan-2-one having the structural formula:

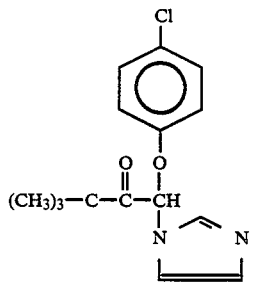

which is prepared by reacting 1-bromo-1-(4-chlorophenoxy)-3,3-dimethylbutan-2-one with imidazole dissolved in acetonitrile as disclosed in U.S. Pat. Nos. 3,812,142 and 3,903,287 the disclosures of which are incorporated herein by reference. This imidazolyl ketone may be obtained from the Bayer Company and is a water insoluble crystalline powder having a melting point of 94.5°–97.8° C. It has been found that this antimicrobial agent is nonionic as a result of steric hindrance effects. The effective concentration of the antimicrobial agent useful in the present aqueous shampoo vehicle is preferably about 0.1–2% by weight of the total shampoo. It has further been found that the imidazolyl compound must first be solubilized in a nonionic medium prior to the addition of ionic materials thereto.

The shampoo vehicle constitutes about 70–95% water, preferably deionized water, containing a low pH surfactant system of about pH 4–5 comprising about 6–25% by weight of anionic surfactant and minor amounts of nonionic and/or amphoteric and/or cationic surfactants.

More specifically, the surfactant system in the present antidandruff shampoo may be a combination of anionic and nonionic surfactants in a weight ratio of 14/3 anionic/nonionic surfactant; an anionic and amphoteric surfactant combination in a weight ratio of 8/2 anionic/amphoteric surfactant; an anionic surfactant combined with amphoteric and cationic surfactants in a weight ratio of 8/2/0.2 anionic/amphoteric/cationic; an anionic surfactant in combination with a nonionic, amphoteric and cationic surfactants in a weight ratio of 8/1/1/0.1 anionic/nonionic/amphoteric/cationic; etc.

The composition of the shampoo bases, i.e., the surfactant systems, has little effect on Climbazole deposition to the skin. However, the addition of about 4% triethanolamine myristate (TEAM), to a 14/3 anionic sodium lauryl polyethoxy ether sulfate (SLES)/nonionic cocodiethanolamide (CDEA) system did increase the deposition of Climbazole.

In vivo hand soaking experiments were used to determine the effects of the particular surfactant system, the pH of the surfactant system, and the level of the Climbazole in the composition, on the amount of the Climbazole deposition to the skin. The experiments were conducted using volunteers, whose hands were soaked in the test solution which were 10% aqueous solutions of Climbazole shampoos. The Climbazole deposited onto the skin of the hands was then eluted with methanol. The methanol rinsings were analyzed using High Performance Liquid Chromotography (HPLC).

The influence of surfactant systems on the deposition of Climbazole was investigated. High active (14/3, SLES/CDEA) and low active (8/1, 8/2 SLES/CDEA) formulations, with or without the addition of cationic polymer were included as shown in Table I. Full formulation details of all the cited surfactant systems appear in Example 1 to 6 hereinafter set forth.

TABLE I

Climbazole Deposition to Skin of the Hand - Expressed as Total Amount

| Surfactant System | Climbazole Level % | pH | Climbazole Deposited (Micrograms) |
|---|---|---|---|
| A. 14/3 SLES/CDEA | 1.0 | 7.40 | 390 |
| B. 8/1 SLES/CDEA | 0.5 | 7.50 | 360 |
| C. 8/2 SLES/BETAINE | 0.5 | 7.35 | 283 |
| D. 8/1/1/0.1 SLES/CDEA/BETAINE/MERQUAT 550 | 0.5 | 7.30 | 430 |
| E. 8/2/0.2 SLES/BETAINE/MERQUAT 550 | 0.5 | 7.30 | 304 |
| F. 14/3/4 SLES/CDEA/TEA MYRISTATE | 1.0 | 8.0 | 456 |
| G. 8/1 SLES/CDEA | 0.5 | 4.0 | 1016 |

These results clearly show that the low pH 4.0 surfactant system (G) gave significantly higher deposition of 1016 ug Climbazole than all the other test shampoos having a pH of 7.0–8.0, and an initial Climbazole content of 0.5–1.0%. Furthermore, this low pH composition (G) gave a deposition level about 2.8 items higher than the same formula at pH 7.5 (B). The presence of triethanolamine myristate (F) in the surfactant system gave significantly higher values than the same surfactant system without TEAM (A) as well as the B to E systems. This suggests that the presence of the TEA myristate does improve the deposition of Climbazole. The substantivity of soap may affect Climbazole deposition.

The effect of varying both pH and Climbazole concentration is shown in Table II, using the same clinical test as described above. All of the test surfactant systems were 14/3, SLES/CDEA containing varying amounts of Climbazole and formulated at various pHs.

TABLE II

Climbazole Deposition to Skin in Micrograms (ugs)

| Surfactant System | Climbazole Level (%) | pH | Climbazole Deposited (micrograms) |
|---|---|---|---|
| A | 0.5 | 4.0 | 562 |
| B | 0.5 | 7.5 | 162 |
| C | 2.0 | 4.0 | 2402 |
| D | 2.0 | 7.5 | 480 |
| E | 1.25 | 5.75 | 588 |

These results clearly show that the pH 4 compositions (A and C) gave significantly higher deposition levels than the corresponding pH 7.5 compositions (B and D respectively). The mean deposition level from the 2.0% Climbazole at pH 7.5 (D) was 480 and that from the same shampoo at pH 4.0 (C) was 2402 ug, 5 times higher. Likewise the deposition level from the 0.5% Climbazole level at pH 7.5 (B) was 162 ugs, and that from the 0.5 Climbazole at pH 4 (A) was 562 ugs, 3 times higher. Composition E containing 1.25% Climbazole at pH 5.75 had a deposition level of 588 ugs which is higher than the 2.0% pH 7.5 composition (D); and slightly higher than the 0.5% pH 4.0 composition A. Thus, a shampoo containing 0.5% Climbazole at pH 4.0 is capable of depositing the equivalent amount of Climbazole as a 2.0% pH 7.5 shampoo. This represents a simple cost-effective method of improving the performance of 0.5% Climbazole shampoo.

The effects of both pH and Climbazole concentration on deposition to the skin from shampoos are shown in Table III, using the same clinical test afore described with reference to the data in Tables I and II.

TABLE III

| Surfactant System | Climbazole Level (%) | pH | Climbazole Deposited (ugs) |
|---|---|---|---|
| A. 14/3 SLES/CDEA | 0.5 | 4.04 | 938 |
| B. 14/3 SLES/CDEA | 0.5 | 5.05 | 645 |
| C. 14/3 SLES/CDEA | 0.5 | 6.02 | 298 |
| D. 14/3 SLES/CDEA | 1.0 | 3.98 | 1579 |
| E. 14/3 SLES/CDEA | 1.0 | 5.12 | 917 |
| F. 14/3 SLES/CDEA | 1.0 | 6.06 | 629 |
| G. 14/3 SLES/CDEA | 1.0 | 7.09 | 393 |
| H. 14/3 *TEALS/CDEA | 0.5 | 3.94 | 1249 |
| I. 14/3 SLES/CDEA | 2.0 | 4.0 | 4435 |
| J. 14/3 SLES/CDEA | 2.0 | 4.99 | 2713 |
| K. 14/3 SLES/CDEA | 2.0 | 7.25 | 978 |

*triethanolammonium lauryl sulfate

These results clearly show that 2% Climbazole at pH 4 (I) gave significantly higher deposition than all the other test shampoos. The 2% Climbazole at pH 4.99 (J) and the 1% Climbazole at pH 3.98 (D) were better than all the other compositions except for the I composition. The TEALS/CDEA BASE (H) containing 0.5% Climbazole at pH 3.94 gave significantly higher deposition than the SLES/CDEA base also containing 0.5% Climbazole at pH 5.05 (B) and pH 6.02 (C); and the 1% Climbazole at pH 7.09 (G) and at pH 6.06 (F) and a pH 5.12 (E). The 2.0% Climbazole pH 4.0 variant (I) gave a mean deposition level of 4435 ug, which was 4.7 times higher than the 0.5% Climbazole, pH 4.04 variant with a mean deposition of 938 ug (A).

The unexpected beneficial effects of reducing the pH are apparent from the deposition results at all levels of Climbazole. The mean deposition result from the 2% pH variant (4435 ugs) indicates that this shampoo composition would be more effective in controlling dandruff either by reducing the dandruff more quickly or by the effects persisting after reverting to a non-antidandruff shampoo.

The 14/3 TEALS/CDEA formulation with 0.5% Climbazole at pH 3.94, gave directionally higher deposition levels than the SLES/CDEA version at pH 4.04. The presence of TEALS is the most obvious difference in these two formulae however hydroxypropylmethyl cellulose (Methocell E4M) was used as the thickening agent since sodium chloride does not sufficiently build viscosity in a TEALS based formulation. The increased deposition level could be due to the presence of the Methocell which is a polymer and may entrap, or complex with the Climbazole molecule. Alternatively, the Climbazole molecule could behave differently with TEALS at low pH. As Climbazole appears to be behaving as a cationic molecule at low pH (6), it may well complex with the anionic material present in the formulation. This complex may then deposit onto the skin.

This series of experiments has demonstrated that the amount of Climbazole adhering to the skin from a shampoo can be greatly increased by making simple changes to the formulation. Experiments have shown that pH and Climbazole concentration have the most dramatic effect on Climbazole deposition to the skin of the hands. The effect of lowering the pH of the shampoo from 7.5 to 4.0 increases the amount of Climbazole adhering to the skin by as much as 400%. This occurs at Climbazole concentrations from 0.5% to 2.0%. The effect was evident in both 14/3 SLES/CDEA, and in lower active products of the 8/1 and 8/2 type. An increase in Climbazole concentration in a shampoo increases the amount deposited onto the skin. This increased deposition occurs independently of the pH of the shampoo.

The 14/3, SLES/CDEA surfactant system shampoos containing 0.25-2.0% Climbazole at pH's between 4 and 7 were aged for 12 months at room temperature to determine the stability of said liquid shampoos.

There was little change in these variants in terms of pH and percentage anionic at room temperature. Results of the sample aged at 49° C. are similar and again there is little evidence of autohydrolysis. There was a change in viscosity, however, with a dramatic rise in all shampoos below pH 5.0. The exception to this is in the 2% Climbazole variants where the viscosity decreased after only six weeks ageing at both room temperature and 49° C. A drop in viscosity also occurred with the TEALS/CDEA variant below pH 5.0. Above this pH the TEALS formulae appear stable.

The levels of Climbazole, as analyzed by HPLC, appear to be remarkably stable, even at the 2% level when aged at 49° C.

An 8/1, SLES/CDEA surfactant system containing 0.5% Climbazole at pH 4 and pH 5 using a buffered system of $Na_2HPO_4.2H_2O$/citric acid or a 75/25 $H_2O$/phosphate buffer to replace the distilled water, also provide stable shampoo compositions upon aging. Magnesium lauryl sulfate or magnesium lauryl ether sulfate in an 8/1 CDEA surfactant system containing 0.5% Climbazole at pHs of 4 and 5 also provide stable shampoo compositions upon aging.

The primary surfactant in the surfactant system of present novel antidandruff shampoo is the anionic surfactant which is present in an amount of about 6-25% by weight of the composition. Preferably, the anionic surfactant is a water soluble sulfate or sulfonate salt having an alkyl radical of 10-18 carbon atoms.

The anionic sulfate or sulfonate surface active agent provides strong cleaning action to the composition. Examples of suitable anionic detergents which fall within the scope of this anionic detergent class include the water-soluble salts, e.g., the sodium, ammonium and alkylolammonium salts, of the water-soluble sulfated and sulfonated synthetic detergents having an alkyl radical of 10-18 carbon atoms in their molecular structure. (The term alkyl includes the alkyl portion of the higher acyl radicals.)

A preferred group of anionic surfactants may be represented by the following general formula:

wherein $R_1$ is an alkyl radical having 10–18 carbon atoms, n is an integer having the value of 0–5, and M is an alkali metal, ammonium, alkylolammonium or an organic amine. Typically preferred anionic surfactants are sodium lauryl polyethenoxy ether sulfate (SLES-2EO) & triethanolamine lauryl sulfate.

The particular anionic detergent salt will be suitably selected depending upon the particular formulation and the proportion therein. Suitable salts include the ammonium, substituted ammonium (mono-, di- and triethanolammonium), and alkali metal (such as sodium and potassium) salts. Preferred salts are the ammonium, triethanolammonium, sodium and potassium salts of the higher alkyl sulfates and the $C_8$–$C_{18}$ acyl sarcosinates.

The surfactant system includes minor amounts of at least one supplemental water soluble surfactant selected from the group consisting of nonionic, amphoteric, and cationic surfactants, and mixtures thereof, in a total amount of about 1–7% by weight.

The nonionic surfactant in the shampoo surfactant system of the present invention is a fatty acid mono- or di-ethanolamide in an amount of about 1–5% by weight of the composition. The ethanolamide component of the instant liquid shampoo functions primarily as a foam booster. Useful compounds in this group include mono- and di-ethanolamides of higher fatty acids having about 8–18 carbon atoms. Specific examples of suitable ethanolamides include cocomonoethanolamide, cocodiethanolamide, lauric myristic diethanolamide, lauric monoethanolamide, or combinations thereof.

The amphoteric surfactant component of the instant liquid shampoo formulation provides increased viscosity, mild cleansing and mild conditioning action to the composition, and is selected from the group consisting of betaines, sulfobetaines, amidobetaines, amidosulfobetaines and mixtures thereof, having the following general formula:

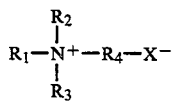

wherein $R_1$ is an alkyl group having 10 to about 20 carbon atoms, preferably 12 to 16 carbon atoms or the amido radical:

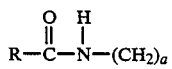

wherein R is an alkyl group having about 10 to 20 carbon atoms and "a" is the integer 1 to 4; $R_2$ and $R_3$ are each alkyl groups having 1 to 3 carbons and preferably 1 carbon; $R_4$ is an alkylene or hydroxyalkylene group having from 1 to 4 carbon atoms and, optionally, one hydroxyl group; and X is an anion selected from the group consisting of $SO_3$= and $COO$=. A typically preferred amphoteric surfactant is cocoamidepropyl betaine. The amphoteric surfactant constitutes about 1–5% by weight of the shampoo composition.

The supplemental cationic surfactant in the surfactant system of the present antidandruff shampoo constitutes about 0.05–0.5% by weight of a polymeric quaternary ammonium salt consisting of acrylamide and dimethyl diallyl ammonium chloride monomers wherein the dimethyl diallyl ammonium chloride monomer has the following repeating structure:

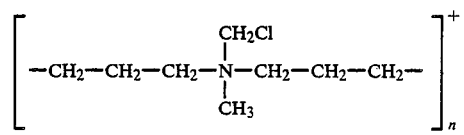

wherein n is an integer in the range of 500 to 1000. These polymerized quaternized ammonium compounds provide excellent conditioning properties are water soluble and retain their cationic activity in the shampoo composition. This compound is also known as polyquaterium 7 and is commercially available as Merquat 550 from Merck & Co., Inc., Rahway, NJ.

In addition to the previously mentioned constituents of the liquid shampoo one may also employ normal and conventional adjuvants, provided they do not adversely affect the properties of the shampoo. Thus, there may be used various coloring agents and perfumes, ultraviolet light absorbers such as the Uvinuls, which are products of GAF Corporation, preservatives such as formaldehyde or hydrogen peroxide; pearlescing agents and opacifiers; solvents, such as ethanol, glycerin and glycols (ethylene glycol is useful as a clarifying agent, to prevent high and low temperature clouding of desirably clear shampoos); lubricants, such as mineral oil and higher fatty alcohols, e.g. cetyl alcohol, stearyl alcohol; sequestering agents such as EDTA tetrasodium salt, thickening agents such as hydroxypropyl methyl cellulose (Methocel 34M) and salts such as sodium chloride, etc. The proportion of such adjuvant material, in total, will normally not exceed 5% of the shampoo.

The present shampoos are readily made by simple mixing methods from readily available components which, on storage, do not adversely affect the entire composition. However, it is essential that the imidazolyl compound be first mixed with the nonionic component such as the ethanolamide (if present), prior to the addition of the amphoteric, cationic, and anionic surfactants. However, in the absence of a nonionic surfactant, the Climbazole can also be mixed with an aqueous solution of the amphoteric betaine prior to the addition of the anionic surfactant. Thus, the products are capable of being made in desired clear form or in opaque or opalescent form. The viscosities are adjustable by changing the total percentage of active ingredients and by modifying the percentages of thickening agent, sodium chloride and other adjuvants. The viscosity of the shampoo will normally be about that of glycerin at room temperature, e.g., about 1,000 centipoises, but the viscosity may be in the broader ranges of 250–2,000 and 50–5,500 centipoises. Its viscosity may approximate those of commercially acceptable shampoos now on the market. Instead of measuring viscosity directly, as by a Brookfield LVF viscometer, one may employ standard laboratory flow tests, in which flow times through a restriction or tube length under a reproducible head are measured in seconds, utilizing a Raymond tube. Viscosities may preferably range from 10–135 seconds and up to 300 or 400 seconds. The shampoo itself remains stable on storage for lengthy periods of time, without color changes or settling out of any insoluble materials.

Chemical test have shown that these novel products have unexpectedly superior antidandruff control properties over prior art antidandruff shampoos such as Head & Shoulders. The major factor affecting the Climbazole-containing shampoo is the pH. A reduction of pH from 7 (Standard pH) to 4.0, greatly increases the amount of Climbazole which adheres to the skin, potentially by as much as 400%. The increase in Climbazole deposition on the scalp is shown to increase the effectiveness of reducing dandruff. The results showed that a 2% Climbazole, pH 5.5 shampoo was more effective at reducing dandruff than standard 1% Climbazole pH 7.0 shampoo.

Clinical tests were used to investigate the effectiveness of both 1% and 2% Climbazole shampoos at pH 4.0, compared to the standard 1% Climbazole pH 7.0 shampoo and the Head and Shoulders shampoo, to demonstrate the relationship between the increased deposition of Climbazole to the skin at low pH and increased antidandruff efficacy.

Volunteer panelists who are dandruff sufferers followed a twice-weekly wash regime which lasted for four weeks, a total of seven shampooings. Statistical analysis was carried out on the percentage reduction in dandruff, using a scoring system including the scalp dandruff score and the hair dandruff score. Both the area of the scalp covered with dandruff and its severity are taken into account. The scalp dandruff score=area×severity. The severity of the dandruff on the scalp is rated as follows:

0—Non visible
1—Small flakes resembling a course greyish white powder
2—Intermediate
3—Large flakes loosely attached to scalp and giving an irregular whitish surface
4—Intermediate
5—Flakes adhered to scalp as white or yellow plates.
3—Small flakes, as in 1, adhering to scalp as in 5.

The head is divided into 4 areas and the proportion of the scalp area covered with dandruff is rated as follows:
1—up to ¼
2—¼ to ½
3—½ to ¾
4—over ¾

The dandruff on the hair is rated as follows:
0—Virtually non visible
1—
2—Moderate flaking
3—
4—Very heavy flaking At the end of the treatment period, the number of panelists and the % of panellists achieving a reduction in dandruff of 80% or more is recited in Table V. Full formulation details of the test shampoos appear in Examples 7 to 10 hereinafter set forth.

TABLE V

| Shampoo | 80% Reduction in Dandruff | |
|---|---|---|
| | Number of Panelists | % |
| Placebo (control) | 0 of 17 | 0 |
| Head and Shoulders[1] | 2 of 17 | 12 |
| 1% Climbazole pH 7 | 4 of 17 | 24 |
| 1% Climbazole pH 4 | 9 of 17 | 53 |
| 2% Climbazole pH 4 | 12 of 17 | 70 |

(1. 65.5% water, 4.1% cocomonoethanolamide, about 20.9% ammonium lauryl ethenoxy/ammonium lauryl sulfate (av. EO—2), 0.4% sodium chloride and 1.0% zinc pyrithione).

Both the 1% and 2% Climbazole pH 4 shampoos were superior to the pH 7.0 shampoo and the "Head and Shoulders" shampoo at reducing dandruff. The 2% Climbazole shampoo showed directionally better dandruff reduction than the 1% variant. However, it is suggested that the 1% Climbazole is the optimum level for cost efficiency, and may be used as a frequent use antidandruff shampoo.

The following examples illustrate but do not limit the invention. Unless otherwise mentioned, all percentages in the examples and elsewhere in the specification are by weight and all temperatures are in °C.

LIQUID ANTIDANDRUFF SHAMPOOS

Example 1

| 14/3 SLES/CDEA | % |
|---|---|
| SLES 2EO (28% AI in water) | 50.0 |
| CDEA/Glycerine 75/10 | 3.0 |
| Climbazole | 1.0 |
| Formalin | 0.1 |
| EDTA (Na4 salt) 30% | 0.26 |
| Perfume | 0.40 |
| Distilled water q.s. | 100.0 |
| Salt | as required |

The salt is added to control viscosity of the liquid shampoo. The pH of the various batches are adjusted with either 50% citric acid or 10% sodium hydroxide to the desired pH.

The Climbazole and the CDEA/glycerin are mixed until homogeneous and clear. The aqueous solution of SLES.2EO is added with agitation. Water, formalin, EDTA, salt (if used) and perfume are added and continuously agitated to form a clear liquid.

The resultant product at pH 3.98 exhibited superior antidandruff properties substantiated by a mean deposition of 1579 micrograms (ug) Climbazole compared to 916.5 ug at pH 5.12; 628.5 ug at pH 6.0, and 393 ug at pH 7.09. The pH 4 shampoo controls the dandruff more quickly and/or prolongs the persistence of the antidandruff effects after reverting to a non-antidandruff shampoo.

Two 10 ml portions of shampoo were allocated to each panellist to wash his own hair. The general procedure consists of wetting the hair with warm tap water, applying the shampoo to the hair, lathering it into the hair, rinsing with warm tap water, re-lathering with additional shampoo, and rinsing the shampoo from the head, after which the hair is towel dried, and dried further with an automatic hair dryer if desired. It is preferred that the hair be shampooed twice weekly to remove the dandruff more quickly.

Example 2

| 8/2 SLES/Betaine | % |
|---|---|
| SLES 2EO (28% AI in water) | 28.57 |
| Cocoamidopropyl betaine | 2.0 |
| Climbazole | 0.50 |
| Formalin | 0.10 |
| EDTA (Na4 salt) 30% | 0.26 |
| Food blue 2 (1%) | 0.25 |
| Perfume | 0.40 |
| Distilled water q.s. | 100.0 |
| Salt | As required |

The Climbazole is mixed with an aqueous solution of the betaine, followed by the addition with agitation of the aqueous solution of SLES 2EO. The water, formalin, EDTA, food blue, perfume and salt (when needed) are added with continuous mixing to form a clear blue liquid.

Example 3

| 8/2/0.2 SLES/Betaine/Merquat | % |
|---|---|
| SLES 2EO (28% AI in water) | 28.57 |
| Cocoamidopropyl betaine | 2.0 |
| Merquat 550 (8% AI) | 2.50 |
| Climbazole | 0.50 |
| Formalin | 0.10 |
| Perfume | 0.40 |
| EDTA (Na4 salt) 30% | 0.26 |
| Food Blue 2 (1%) | 0.25 |
| Distilled water q.s. | 100.0 |
| Salt | As required |

This product is prepared in accordance with the procedure of Example 2, except that the Merquat is added.

Example 4

| 8/1/1/0.1 SLES/CDEA/Betaine/Merquat | % |
|---|---|
| SLES 2EO (28% AI in water) | 28.57 |
| CDEA/Glycerine 75/10 | 1.0 |
| Cocoamidopropyl betaine | 1.0 |
| Merquat 550 (8% AI) | 1.25 |
| Climbazole | 0.5 |
| Formalin | 0.1 |
| EDTA (Na4 salt) 30% | 0.26 |
| Perfume | 0.40 |
| Food blue 2 (1%) | 0.25 |
| Distilled water q.s. | 100.0 |
| Salt | As required |

The Climbazole is mixed with the CDEA/glycerin followed by the addition of the betaine with agitation, followed by the SLES with agitation and the Merquat with mixing, and lastly adding the water and all the other ingredients with agitation to form a liquid shampoo.

Example 5

| 14/3 TEALS/CDEA | % |
|---|---|
| Triethanolamine lauryl sulfate (40% AI in water) | 34.56 |
| CDEA/Glycerine 75/10 | 3.0 |
| Climbazole | 0.50 |
| Methocell E4M | 0.75 |
| Formalin | 0.10 |
| EDTA (Na4 salt) 30% | 0.26 |
| Perfume | 0.60 |
| Distilled water q.s | 100.0 |

The shampoo of Example 5 is made by first dissolving the Climbazole in the nonionic component, CDEA/glycerine, Methocell is dissolved separately in approximately 80% of the total water, then added to the Climbazole/nonionic mixture along with the TEALS and the remaining water. The remainder of the ingredients are then added.

Example 6

| 14/3/4 SLES/CDEA/TEA Myristate | % |
|---|---|
| Triethanolamine (99%) | 1.60 |
| Myristic acid | 2.50 |
| SLES 2EO (28% AI in water) | 50.0 |
| Euperlan PK 771 | 4.0 |

| 14/3/4 SLES/CDEA/TEA Myristate | % |
|---|---|
| CDEA/Glycerine 75/10 | 3.0 |
| Climbazole | 3.0 |
| Perfume | 0.40 |
| Food blue 2 (1%) | 0.25 |
| Formalin | 0.10 |
| EDTA (Na4 salt) 30% | 0.26 |
| Salt | as required |
| Distilled water q.s. | 100.0 |

The shampoo of Example 6 is made by first heating the water, TEA and myristic acid to 65° C. and stirring until a homogeneous mixture is obtained. SLES and Euperlan PK771 are then added to this mixture. (Euperlan PK771 is a cold mix opacifier available from Henkel which contains SLES and imparts a pearlescent appearance to the shampoo.) Climbazole is then dissolved separately in the CDEA/glycerine component and added. The remainder of the ingredients are added after the mixture has cooled.

Example 7

| | % |
|---|---|
| SLES 2EO (28% AI in water) | 47.14 |
| CDEA/Glycerine | 3.0 |
| Euperlan PK 771 | 4.0 |
| Climbazole | 1.0 |
| Formalin | 0.1 |
| EDTA 30% (Na4 salt) | 0.26 |
| Perfume | 0.40 |
| Food Blue 2 (0.1%) | 0.20 |
| Salt | 1.00 |
| Water | 42.90 |
| Viscosity = 3000 cps | |
| pH = 7.9 | |

The product is prepared in accordance with the procedure of Example 1.

Example 8

| | % |
|---|---|
| SLES 2EO (28% AI in water) | 47.14 |
| CDEA/Glycerine | 3.0 |
| Euperlan PK 771 | 4.0 |
| Climbazole | 1.0 |
| Formalin | 0.1 |
| EDTA 30% (Na4 salt) | 0.26 |
| Food Blue 2 (0.1%) | 0.20 |
| Perfume | 0.40 |
| Water | 43.90 |
| Viscosity = 3800 cps | |
| pH = 4.0 | |

The product is prepared in accordance with the procedure of Example 1.

Example 9

| | % |
|---|---|
| SLES 2EO (28% AI in water) | 47.14 |
| CDEA/Glycerin | 3.0 |
| Euperlan PK 771 | 4.0 |
| Climbazole | 2.0 |
| Formalin | 0.1 |
| EDTA 30% (Na4 salt) | 0.25 |
| Food Blue 2 (0.1%) | 0.26 |
| Perfume | 0.20 |
| Distilled water | 42.90 |
| pH = 4.0 | |

|  | % |
| --- | --- |
| Viscosity = 5,500 cps |  |

This product is prepared in accordance with the procedure of Example 1.

The shampoos of Examples 8 and 9 having a pH of 4 are superior in reducing dandruff to the shampoo of Example 7 having a pH of 7.9.

Example 10

|  | |
| --- | --- |
| SLES 2EO (28% AI in water) | 47.14 |
| CDEA/Glycerine | 3.00 |
| Euperlan PK 771 | 4.00 |
| Climbazole | 2.00 |
| Formalin | 0.10 |
| EDTA 30% (Na$_4$ salt) | 0.26 |
| Perfume | 0.40 |
| Food Blue 2 (0.1%) | 0.20 |
| Distilled water to pH 5.50 | 100.00 |

The pH was adjusted using citric acid solution. The viscosity increased with a lowering of pH and no salt was needed.

This shampoo gave significantly greater dandruff reduction than the standard 14/3, 1% Climbazole, pH 7 shampoo of Example 7. This effect occurred with a twice-weekly wash regime over a period of 4 weeks. There was also evidence of a trend for this shampoo to reduce dandruff at an increased rate compared to the Example 7 shampoo.

The invention has been described with respect to various examples and embodiments but it is not to be limited to these because it is evident that one of skill in the art with the present application before him will be able to utilize substitutes and equivalents without departing from the spirit of the invention.

We claim:

1. A homogenous liquid antidandruff shampoo composition comprising about 0.1-2.0% by weight of 1-imidazolyl-1-(4-chlorophenoxy)-3,3-dimethylbutan-2-one (Climbazole) solubilized in an aqueous vehicle containing a low pH surfactant system which is adjusted with an agent to about pH 4 to 5, said surfactant system comprising an anionic surfactant as the primary surfactant and minor amounts of a supplemental surfactant selected from the group consisting of nonionic, amphoteric, and cationic surfactants and mixtures thereof.

2. The composition according to claim 1, wherein the aqueous vehicle constitutes about 70-95% by weight.

3. The composition according to claim 2, wherein the anionic surfactant constitutes about 6-25% by weight and the supplemental surfactant or mixture of surfactants constitutes about 1-7% by weight.

4. The composition according to claim 3, wherein the surfactant system comprises a combination of anionic and nonionic surfactants in a weight ratio of 14/3, anionic/nonionic surfactant.

5. The composition according to claim 3, wherein the surfactant system comprises a combination of anionic and amphoteric surfactants in a weight ratio of 8/2, anionic/amphoteric surfactant.

6. The composition according to claim 3, wherein the surfactant system comprises a combination of anionic, amphoteric and cationic surfactants in a weight ratio of 8/2/0.2, anionic/amphoteric/cationic surfactant.

7. The composition according to claim 3, wherein the surfactant system comprises a combination of anionic, nonionic, amphoteric and cationic surfactants in a weight ratio of 8/1/1/0.1, anionic/nonionic/amphoteric/cationic surfactant.

8. The composition according to claim 5, additionally containing triethanolamine myristate.

9. The composition according to claim 3, wherein the anionic surfactant is a water soluble sulfate or sulfonate salt having an alkyl radical of 10-18 carbon atoms.

10. The composition according to claim 9, wherein the anionic surfactant is represented by the formula:

$$R_1-O(CH_2CH_2O)_nSO_3M,$$

wherein $R_1$ is an alkyl radical having 10-18 carbon atoms, n is an integer having a value of 0-5, and M is an alkali metal, ammonium, alkylol ammonium or an organic amine.

11. The composition according to claim 10, wherein the anionic surfactant is sodium lauryl ethenoxy ether sulfate containing 2-ethoxy radicals per molecule.

12. The composition according to claim 4, wherein the nonionic supplemental surfactant is a mono- or di-ethanolamide of a higher fatty acid having 8 to 18 carbon atoms, in an amount of about 1-5% by weight.

13. The composition according to claim 12, wherein the nonionic surfactant is cocodiethanolamide.

14. The composition according to claim 5 wherein the amphoteric surfactant is selected from the group consisting of betaines, sulfobetaines, amidobetaines, amidosulfobetaines and mixtures thereof, in an amount of about 1-5% by weight.

15. The composition according to claim 14, wherein the amphoteric surfactant is cocoamidopropyl betaine.

16. The composition according to claim 3, wherein the cationic surfactant is a polymeric quaternary ammonium salt consisting of acrylamide and dimethyl diallyl ammonium chloride monomers, in an amount of about 0.05-0.5% by weight.

17. The composition according to claim 4, containing 1% Climbazole and having a pH 4.

18. The composition according to claim 4 containing 2% Climbazole and having a pH 4.

19. A method of removing dandruff from the scalp and hair comprising shampooing with the liquid composition of claim 1 at least twice weekly.

20. A composition according to claim 1, wherein the agent for adjusting the pH is a strong base.

21. A composition according to claim 1, wherein the agent for adjusting the pH is a strong acid.

* * * * *